(12) United States Patent
Konishi et al.

(10) Patent No.: US 9,375,508 B2
(45) Date of Patent: Jun. 28, 2016

(54) WATER DISINTEGRATABLE ABSORBER AND ABSORBENT ARTICLE

(75) Inventors: Takayoshi Konishi, Kagawa (JP); Toshiyuki Tanio, Kagawa (JP); Kiyoko Nishimura, Kagawa (JP)

(73) Assignee: Unicharm Corporation, Ehime (JP)

( * ) Notice: Subject to any disclaimer, the term of this patent is extended or adjusted under 35 U.S.C. 154(b) by 45 days.

(21) Appl. No.: 14/347,378

(22) PCT Filed: Aug. 13, 2012

(86) PCT No.: PCT/JP2012/070641
§ 371 (c)(1),
(2), (4) Date: Mar. 26, 2014

(87) PCT Pub. No.: WO2013/046967
PCT Pub. Date: Apr. 4, 2013

(65) Prior Publication Data
US 2014/0243771 A1    Aug. 28, 2014

(30) Foreign Application Priority Data
Sep. 30, 2011  (JP) ................................ 2011-218013

(51) Int. Cl.
| | |
|---|---|
| *A61F 13/15* | (2006.01) |
| *A61L 15/62* | (2006.01) |
| *A61L 15/22* | (2006.01) |
| A61F 13/534 | (2006.01) |
| A61F 13/53 | (2006.01) |

(52) U.S. Cl.
CPC ........... *A61L 15/62* (2013.01); *A61F 13/15211* (2013.01); *A61L 15/22* (2013.01); *A61F 2013/15235* (2013.01); *A61F 2013/530313* (2013.01); *A61F 2013/53481* (2013.01); *A61F 2013/530795* (2013.01)

(58) Field of Classification Search
CPC ........... A61F 13/5349; A61F 13/53481; A61F 13/53445; A61F 13/430313; A61F 13/530795; A61F 13/53463; A61F 13/53472
See application file for complete search history.

(56) References Cited

U.S. PATENT DOCUMENTS

| | | | |
|---|---|---|---|
| 6,635,799 B1 * | 10/2003 | Osborn et al. | ................ 604/367 |
| 8,907,155 B2 * | 12/2014 | Wang et al. | ................... 604/364 |

(Continued)

FOREIGN PATENT DOCUMENTS

| | | |
|---|---|---|
| EP | 1 118 314 A2 | 7/2001 |
| EP | 1 493 414 A1 | 1/2005 |

(Continued)

OTHER PUBLICATIONS

International Search Report and Written Opinion from corresponding PCT application No. PCT/JP2012/070641 dated Nov. 6, 2012 (4 pgs).

*Primary Examiner* — Bradley Philips
(74) *Attorney, Agent, or Firm* — Brinks Gilson & Lione (57) ABSTRACT

An absorber and an absorbent article which have excellent leak proof property during use and water disintegratability after disposal. The water disintegratable absorber includes a water disintegratable absorber layer and a water insoluble resin layer. The amount of water absorption of the water disintegratable absorber layer is 300 g/m² or more and tear strength in the plan view direction of the water insoluble resin layer is 0.15 N/40 mm or less in a first direction as well as a second direction that is orthogonal to the first direction.

19 Claims, 2 Drawing Sheets

(56) References Cited

U.S. PATENT DOCUMENTS

| | | |
|---|---|---|
| 2001/0014566 A1 | 8/2001 | Kurata et al. |
| 2001/0021458 A1* | 9/2001 | Campbell et al. ............. 428/508 |
| 2002/0177827 A1* | 11/2002 | Noda et al. .................... 604/364 |
| 2003/0100240 A1* | 5/2003 | Takai et al. .................... 442/408 |
| 2003/0178166 A1 | 9/2003 | Takeuchi et al. |
| 2012/0048916 A1 | 3/2012 | Konishi et al. |
| 2012/0265161 A1* | 10/2012 | Banks et al. .................. 604/372 |

FOREIGN PATENT DOCUMENTS

| | | |
|---|---|---|
| JP | 2001-172850 A | 6/2001 |
| JP | 2001-333933 A | 12/2001 |
| JP | 2003-119654 A | 4/2003 |
| JP | 2007-97924 A | 4/2007 |
| JP | 2009-013521 | 1/2009 |
| JP | 2012-205725 A | 10/2012 |
| WO | WO 92/02199 A1 | 2/1992 |

* cited by examiner

WATER DISINTEGRATABLE ABSORBER AND ABSORBENT ARTICLE

RELATED APPLICATION

This application is a 35 U.S.C. §371 national phase filing of International Patent Application No. PCT/JP2012/070641, filed Aug. 13, 2012, through which and to which priority is claimed under 35 U.S.C. §119 to Japanese Patent Application No. 2011-218013, filed Sep. 30, 2011.

TECHNICAL FIELD

The present invention relates to a water-disintegratable absorber and to an absorbent article comprising the absorber.

BACKGROUND ART

Absorbent articles such as sanitary napkins, diapers and incontinence pads generally contain non-water-disintegratable materials. Used absorbent articles are therefore discarded in stowage boxes provided in toilets, and collected and disposed. However, when used absorbent articles are inadvertently flushed in flush toilets, they can potentially clog the pipes of the flush toilets. Research has therefore been conducted on water-disintegratable materials that can be flushed into flush toilets directly after use, and absorbent articles comprising the water-disintegratable materials.

For example, PTL 1 describes a leakproof sheet for a hygienic pad, wherein a water-repellent layer is stacked on one side of a water-soluble resin sheet, and a water-disintegratable base material is stacked on the other side of the water-soluble resin sheet.

The leakproof sheet described in PTL 1 has a three-layer structure of the water-disintegratable base material, the water-soluble resin sheet and the water-repellent layer, being designed so that the two layers of the water-repellent layer and the water-soluble resin sheet hold absorbed fluids inside a hygienic pad and prevent leakage.

CITATION LIST

Patent Literature

[PTL 1] Japanese Unexamined Patent Publication No. 2001-333933

DISCLOSURE OF THE INVENTION

Technical Problem

However, improvement is desired in conventional absorbers and absorbent articles from the viewpoint of leakproofness during use and water-disintegratability after disposal.

It is therefore an object of the present invention to provide an absorber and absorbent article having excellent leakproofness during use and water-disintegratability after disposal.

Solution to Problem

In order to solve the problems described above, the invention provides a water-disintegratable absorber comprising a water-disintegratable absorbent layer and a water-insoluble resin layer, wherein the water-disintegratable absorbent layer has a water absorption of 300 g/m² or more, and the water-insoluble resin layer has a tear strength of 0.15 N/40 mm or less in first and second directions on a surface of the water-insoluble resin layer, the second direction being perpendicular to the first direction.

The invention further provides an absorbent article comprising a first water-disintegratable sheet that has liquid permeability, a second water-disintegratable sheet, and an absorber situated between the first water-disintegratable sheet and the second water-disintegratable sheet, wherein the absorber is a water-disintegratable absorber according to the invention.

The water-disintegratable absorber of the invention exhibits the following effects during use and after disposal.

[During Use]

Liquids are absorbed by the water-disintegratable absorbent layer. The water absorption of the water-disintegratable absorbent layer (300 g/m² or more) is a sufficient amount of water absorption for commonly used absorbent articles such as sanitary and hygiene products. The water-disintegratable absorbent layer disintegrates by the absorbed liquids and decreases in strength, but the water-insoluble resin layer has water resistance and therefore does not decrease in strength. Consequently, the water-disintegratable absorbent layer is reinforced by the water-insoluble resin layer and retains its form, allowing liquids to be continuously absorbed.

Since the liquids absorbed into the water-disintegratable absorbent layer cannot pass through the water-insoluble resin layer, leakage of the liquids absorbed into the water-disintegratable absorbent layer is prevented by the water-insoluble resin layer. The water resistance of the water-insoluble resin layer is not affected by water in the liquids absorbed into the water-disintegratable absorbent layer and moisture in the air contacted by the water-insoluble resin layer, and therefore the leakproofness of the water-insoluble resin layer is stably maintained.

Thus, the water-disintegratable absorber of the invention exhibits excellent leakproofness.

[After Disposal]

When the water-disintegratable absorber of the invention is disposed, it is subjected to the force of water streams in flush toilets, wastewater treatment tanks, sewage systems and the like. The water stream force causes the water-disintegratable absorbent layer to rapidly disintegrate and disappear. The water-insoluble resin layer has a tear strength of 0.15 N/40 mm or less in first and second directions on a surface of the water-insoluble resin layer, the second direction being perpendicular to the first direction, and disintegrates when subjected to a greater force by a water stream. When the water-disintegratable absorbent layer disappears, the water-insoluble resin layer is also subjected to the water stream force from the side where the water-disintegratable absorbent layer was present, and therefore is easy to disintegrate.

Thus, the water-disintegratable absorber of the invention exhibits excellent water-disintegratability. For example, the water-disintegratable absorber of the invention exhibits water-disintegratability such that the dispersion ratio is 50 mass % or more when shaken in water for 48 hours at a shaking speed of 240 rpm.

The absorbent article of the invention exhibits the following effects in addition to the effects of the water-disintegratable absorber of the invention mentioned above.

In the absorbent article of the invention, liquids that have passed through the first water-disintegratable sheet is absorbed into the water-disintegratable absorbent layer of the water-disintegratable absorber, and leakage of the liquids absorbed into the water-disintegratable absorbent layer is prevented by the water-insoluble resin layer of the water-disintegratable absorber. Since the water-disintegratable absorber of the invention thus exhibits leakproofness by itself, there is no need for the second water-disintegratable sheet of the absorbent article of the invention to be given a leakproof function. The second water-disintegratable sheet may of course be given a leakproof function, which will further increase the leakproofness of the absorbent article of the invention.

Since it is not necessary for the second water-disintegratable sheet to be given a leakproof function, the second water-disintegratable sheet can be given a different function. For example, the second water-disintegratable sheet may be given an aerating function so that the absorbent article of the invention can have reduced mustiness during wear.

Since both the first water-disintegratable sheet and the second water-disintegratable sheet are water-disintegratable, they disintegrate under the force of water streams in flush toilets, wastewater treatment tanks and sewage systems. The absorbent article of the invention therefore completely disintegrates in water.

In a preferred aspect (aspect 1) of the water-disintegratable absorber of the invention, the water-insoluble resin layer has a tear strength of 0.10 N/40 mm or less in first and second directions on a surface of the water-insoluble resin layer, the second direction being perpendicular to the first direction. Aspect 1 improves the water-disintegratability of the water-insoluble resin layer.

In a preferred aspect (aspect 2) of the water-disintegratable absorber of the invention, the water-disintegratable absorbent layer is directly stacked on the water-insoluble resin layer. Aspect 2 improves the water-disintegratability of the water-insoluble resin layer since the water-insoluble resin layer is also directly subjected to water stream force from the side where the water-disintegratable absorbent layer was present.

In a preferred aspect (aspect 3) of the water-disintegratable absorber of the invention, the water-insoluble resin layer is biodegradable. Aspect 3 allows the environmental load to be reduced.

In a preferred aspect (aspect 4) of the water-disintegratable absorber of the invention, the water-insoluble resin layer has a water pressure resistance of 300 mm or more. According to aspect 4, the leakproofness of the water-insoluble resin layer is stably maintained.

In a preferred aspect (aspect 5) of the water-disintegratable absorber of the invention, the water-insoluble resin layer has a water pressure resistance of 300 mm or more after storage for 3 hours under conditions of a temperature of 36° C. and a relative humidity of 90%. According to aspect 5, the leakproofness of the water-insoluble resin layer is stably maintained even in high humidity.

In a preferred aspect (aspect 6) of the water-disintegratable absorber of the invention, the water-disintegratable absorber has a dispersion ratio of 50 mass % or more when shaken in water for 48 hours at a shaking speed of 240 rpm. According to aspect 6, excellent water-disintegratability is exhibited.

In a preferred aspect (aspect 7) of the water-disintegratable absorber of the invention, the water-insoluble resin layer has a thickness of 10 to 15 μm. According to aspect 7, the leakproofness of the water-insoluble resin layer is stably maintained.

In a preferred aspect (aspect 8) of the water-disintegratable absorber of the invention, the water-insoluble resin layer contains polylactic acid as a water-insoluble resin. According to aspect 8, the water-insoluble resin layer is also biodegradable.

In a preferred aspect (aspect 9) of the water-disintegratable absorber of the invention, the water-disintegratable absorbent layer contains water-dispersible fibers and a water-soluble binder. Aspect 9 improves the water-disintegratability of the water-disintegratable absorbent layer.

In a preferred aspect (aspect 10) of the water-disintegratable absorber of the invention, the water-dispersible fibers have a fiber length of 20 mm or less. Aspect 10 improves the water-disintegratability of the water-disintegratable absorbent layer.

In a preferred aspect (aspect 11) of the water-disintegratable absorber of the invention, the water-disintegratable absorbent layer has a fiber basis weight of 30 to 100 g/m² or more. Aspect 11 improves the water-disintegratability of the water-disintegratable absorbent layer.

In the water-disintegratable absorber of the invention, two or more of aspects 1 to 11 may also be combined.

Effect of the Invention

According to the invention, there are provided an absorber and absorbent article having excellent leakproofness during use and water-disintegratability after disposal.

DESCRIPTION OF EMBODIMENTS

There are no particular restrictions on the type and usage of the absorbent article of the invention. For example, absorbent articles include sanitary and hygiene products such as sanitary napkins, diapers, panty liners, incontinence pads and perspiration sheets, which may be for humans or animals other than humans, such as pets. There are no particular restrictions on fluid to be absorbed by the absorbent article of the invention, and for example, it may be liquid excreta or body fluid of a user.

Embodiments of the absorbent article of the invention will now be described, using a panty liner as an example.

Figure 1:
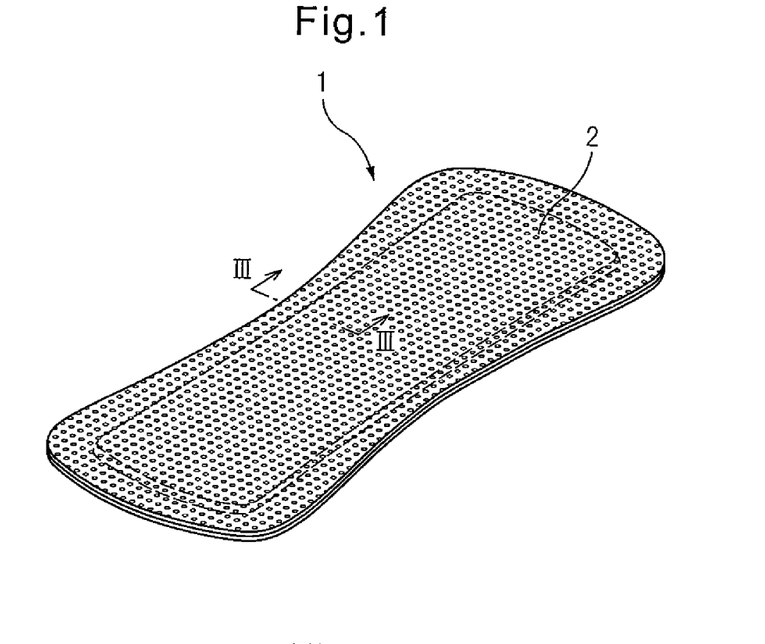
FIG. 1 is a perspective view of a panty liner according to an embodiment of the invention.
Figure 2:
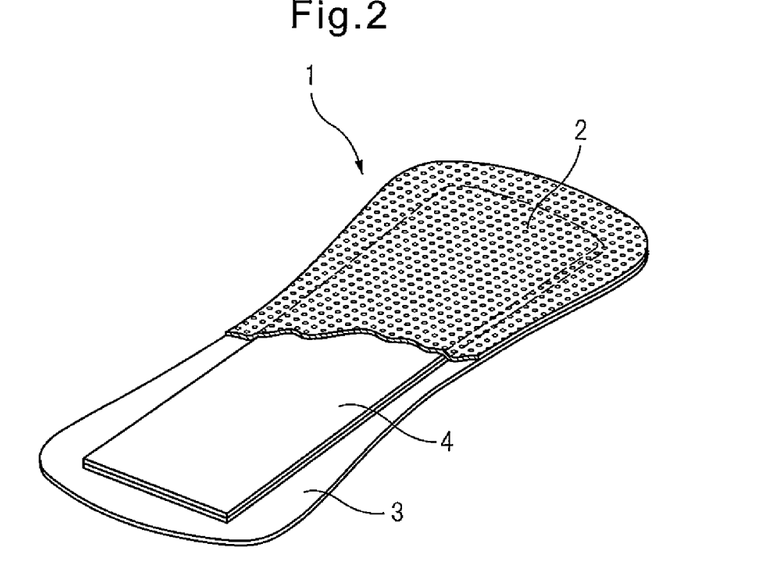
FIG. 2 is a partial cutaway view of the panty liner shown in FIG. 1.
Figure 3:
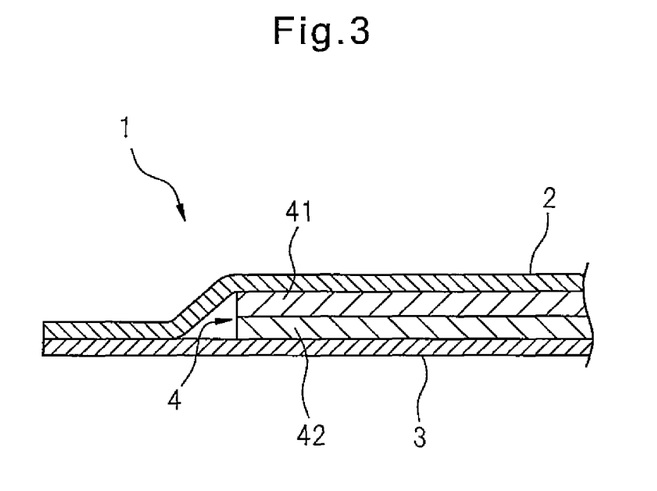
FIG. 3 is a magnified cross-sectional view of FIG. 1 along line III-III.

A panty liner 1 according to one embodiment of the invention comprises, as shown in FIGS. 1 to 3, a top sheet 2, a back sheet 3, and an absorber 4 disposed between the top sheet 2 and the back sheet 3.

The panty liner 1 is worn by a user to absorb liquid excreta of the user (such as menstrual blood, urine and vaginal discharge). The user wears the panty liner 1 in such a manner that the top sheet 2 is located on the skin side of the user, and the back sheet 3 is located on the side of the clothing (underwear) of the user. The liquid excreta of the user permeate into the absorber 4 through the top sheet 2 and are absorbed by the absorber 4.

The top sheet 2 is provided on the side that contacts with the skin of the user, while the back sheet 3 is provided on the side that contacts with the clothing (underwear) of the user.

The top sheet 2 is a sheet that has liquid-permeability and water-disintegratability, while the back sheet 3 is a sheet that has water-disintegratability. The back sheet 3 may also be imparted with a liquid-impermeable property by waterproof treatment. If the back sheet 3 is liquid-impermeable, leakproofness of liquid excreta absorbed into the absorber 4 will be improved. The back sheet 3 preferably has air permeability, in order to reduce mustiness of the panty liner 1 when worn.

The top sheet 2 and back sheet 3 may be water-disintegratable base materials such as water-disintegratable nonwoven fabrics, water-disintegratable tissues or water-disintegratable sheets.

The degree of liquid permeability of the top sheet 2 is not particularly restricted so long as it allows permeation of liquid excreta of the user. The liquid permeability of the top sheet 2 can be appropriately adjusted by modifying the void percentage or forming permeation holes. Examples of sheets with liquid permeability include nonwoven fabrics, woven fabrics, permeation hole-formed resin films and meshed net-like sheets, with nonwoven fabrics being preferred among these. Nonwoven fabrics include, for example, air-through nonwoven fabrics, point bond nonwoven fabrics, spunbond nonwoven fabrics and spun lace nonwoven fabrics, with air-through nonwoven fabrics being preferred among these. An air-through nonwoven fabric has satisfactory liquid permeability because of its high void percentage.

The degree of water-disintegratability of the top sheet 2 and back sheet 3 is not particularly restricted so long as they are capable of dissolving or disintegrating in water either with or without the force of a water stream (for example, the water stream in a flush toilet, wastewater treatment tank or sewage system). The water-disintegratability of the top sheet 2 and the back sheet 3 can be appropriately adjusted by selecting the constituent materials. Examples of water-disintegratable materials include water-dispersible fibers, water-soluble resins, water-soluble cellulose, water-soluble starch and the like. Examples of water-dispersible fibers include hydrophilic fibers such as wood pulp, nonwood pulp (for example, cotton and hemp), rayon, cupra, acetate, cellulose acetate, polyvinyl alcohol fibers, carboxymethyl cellulose fibers and acrylic fibers, and hydrophobic fibers such as polylactic acid fibers, polyester fibers, polyolefin fibers and nylon fibers. The fiber length of the water-dispersible fibers is preferably 20 mm or less and even more preferably 15 mm or less, from the viewpoint of water dispersibility. The lower limit of the fiber length will usually be 2 mm.

Examples of water-soluble resins include polyvinyl alcohol, polyethylene oxide, polypropylene oxide, polyvinylpyrrolidone and polyacrylic acid.

Examples of water-soluble cellulose include methyl cellulose, ethyl cellulose, carboxymethyl cellulose and hydroxyethyl cellulose.

Examples of water-soluble starches include wheat flour starch and corn starch.

The thickness, basis weight and density of the top sheet 2 can be set as appropriate within a range in which the liquid permeability and water-disintegratability of the top sheet 2 is preserved, the thickness being usually 0.1 to 0.5 mm and preferably 0.2 to 0.4 mm, the basis weight being usually 20 to 80 $g/m^2$ and preferably 25 to 60 $g/m^2$, and the density being usually 0.13 to 0.2 $g/cm^3$ and preferably 0.14 to 0.18 $g/cm^3$. If the thickness, basis weight and density are within these ranges, it will be possible to realize a similar degree of soft texture to a nonwoven fabric.

The thickness, basis weight and density of the back sheet 3 can also be set as appropriate within a range in which the water-disintegratability of the back sheet 3 is preserved, the thickness being usually 0.1 to 0.5 mm and preferably 0.2 to 0.4 mm, the basis weight being usually 20 to 80 $g/m^2$ and preferably 25 to 60 $g/m^2$, and the density being usually 0.13 to 0.2 $g/cm^3$ and preferably 0.14 to 0.18 $g/cm^3$. If the thickness, basis weight and density are within these ranges, it will be possible to realize a similar degree of soft texture to a nonwoven fabric.

The absorber 4 comprises a water-disintegratable absorbent layer 41 and a water-insoluble resin layer 42, as shown in FIG. 3, with the water-disintegratable absorbent layer 41 being directly stacked on the water-insoluble resin layer 42. As shown in FIG. 3, the absorber 4 is disposed between the top sheet 2 and the back sheet 3 so that the water-disintegratable absorbent layer 41 is situated on the top sheet 2 side and the water-insoluble resin layer 42 is situated on the back sheet 3 side, and the edges of the top sheet 2 and the back sheet 3 are bonded together.

The water absorption of the water-disintegratable absorbent layer 41 is 300 $g/m^2$ or more. The water absorption ($g/m^2$) of the water-disintegratable absorbent layer 41 can be calculated, for example, by dipping a sample (for example, 100 mm×100 mm) in distilled water for 1 minute and then allowing it to stand for 1 minute on a net for draining, measuring the weight (g) of the sample after water absorption, and determining the difference between that value and the weight of the sample before water absorption. The draining net used may be, for example, a 250 mesh net, and as the 250 mesh net there may be used, for example, a 250 mesh nylon net (N-No. 250HD by NBC Meshtec, Inc.).

The material composing the water-disintegratable absorbent layer 41 can be appropriately selected within a range such that the water-disintegratability and absorption property of the water-disintegratable absorbent layer 41 is maintained. The water-disintegratable absorbent layer 41 may be composed of, for example, water-dispersible fibers and a water-soluble binder. The water-disintegratable absorbent layer 41 is preferably an airlaid nonwoven fabric having water-dispersible fibers anchored with a water-soluble binder. Using such as an airlaid nonwoven fabric will improve the water-disintegratability of the water-disintegratable absorbent layer 41.

The water-dispersible fibers used are not particularly restricted so long as entanglements of the fibers can be loosened in water, and thereby the fibers can disperse in water. The water-dispersible fibers may be hydrophilic fibers or hydrophobic fibers, but some or all of the water-dispersible fibers in the water-disintegratable absorbent layer 41 are hydrophilic fibers. The water-disintegratable absorbent layer 41 contains hydrophilic fibers in an amount commensurate with the absorption property to be exhibited by the panty liner 1. The basis weight of the water-dispersible fibers of the water-disintegratable absorbent layer 41 can be appropriately adjusted within a range in which the water-disintegratability and absorption property of the water-disintegratable absorbent layer 41 is maintained, and it is preferably 30 to 100 $g/m^2$ and more preferably 40 to 80 $g/m^2$.

Examples of water-dispersible fibers include hydrophilic fibers such as wood pulp, nonwood pulp (for example, cotton and hemp), rayon, cupra, acetate, cellulose acetate, polyvinyl alcohol fibers, carboxymethyl cellulose fibers and acrylic fibers, and hydrophobic fibers such as polylactic acid fibers, polyester fibers, polyolefin fibers and nylon fibers, with wood pulp being preferred among these. The fiber length of the water-dispersible fibers is preferably 20 mm or less and even more preferably 10 mm or less, from the viewpoint of water dispersibility. The lower limit of the fiber length will usually be 2 mm.

Examples of the water-soluble binder to be used to anchor the water-dispersible fibers include polyacrylic acid, polyvinyl alcohol, modified polyvinyl alcohol, cellulose derivatives (carboxymethyl cellulose, hydroxyethyl cellulose and the like), starches and saccharides.

The thickness of the water-disintegratable absorbent layer 41 can be appropriately set within a range in which the water-disintegratability and absorption property of the water-disintegratable absorbent layer 41 is maintained, but it will usually be 0.3 to 1.2 mm and is preferably 0.4 to 1.0 mm.

The water-insoluble resin layer 42 is composed of a water-insoluble resin. The water-insoluble resin composing the water-insoluble resin layer 42 is preferably biodegradable. The amount of water-insoluble resin in the water-insoluble resin layer 42 is preferably 100 mass % of the water-insoluble resin layer 42.

Examples of the water-insoluble resin include polylactic acid (PLA), polybutylene succinate (PBS), polybutylene adipate/terephthalate (PBAT), polycaprolactone (PCL), polyhydroxybutyrate (PHB) and polyhydroxyalkanoate (PHA), with polylactic acid being preferred among these. Polylactic acid is biodegradable.

The index of "water insolubility" may be, for example, a solubility of 1.0 g or less in 100 g of purified water at 25° C., and a resin with a solubility of 1.0 g or less in 100 g of purified water in 25° C. may be selected as the water-insoluble resin. For example, water-soluble resins such as carboxymethyl cellulose sodium (CMC) and polyvinyl alcohol (PVA) do not qualify as water-insoluble resins.

The thickness, basis weight and density of the water-insoluble resin layer 42 can be appropriately set within a range in which the water insolubility of the water-insoluble resin layer 42 is maintained. The thickness will usually be 10 to 15 μm and is preferably 10 to 13 μm. If the thickness is within this range, both the functions of leakproofness and water-disintegratability of the water-insoluble resin layer 42 will be effectively exhibited. The thickness of the water-insoluble resin layer 42 can be measured using a commercially available measuring device (for example, a PEACOCK PDN-20 by Ozaki Manufacturing Co., Ltd. (measuring terminal diameter: ϕ8 mm)).

The tear strength of the water-insoluble resin layer 42 is 0.15 N/40 mm or less in both first and second directions on a surface of the water-insoluble resin layer 42, the second direction being perpendicular to the first direction. Thus, the water-insoluble resin layer 42 disintegrates when subjected to greater force than this by a water stream. Here, "N/40 mm" means the tear strength (N) per 40 mm width.

From the viewpoint of improving the water-disintegratability of the water-insoluble resin layer 42, the tear strength of the water-insoluble resin layer 42 is preferably 0.10 N/40 mm or less, and more preferably 0.08 N/40 mm or less, in both the first direction and the second direction perpendicular to the first direction. Also, the aforementioned tear strength of the water-insoluble resin layer 42 is preferably at least 0.03 N/40 mm in order to avoid tearing of the water-insoluble resin layer 42 by the load (for example, body weight) on the panty liner 1 during wear.

The first direction may be, for example, the machine direction (MD direction) during production of the water-insoluble resin layer 42, and the second direction may be, for example, the direction perpendicular to the MD direction (CD direction). Force (for example, stretching force) applied during production of the water-insoluble resin layer 42 can create differences between the tear strength in the MD direction and the tear strength in the CD direction, and if this difference increases, it can make it difficult to achieve balance in the tear strength. Therefore, the water-insoluble resin layer 42 preferably is unstretched (has low orientation) during production.

The tear strength of the water-insoluble resin layer 42 can be measured according to the "Tear test" of JIS K 6772:1994 7.5, for example. The specific procedure is as described in the examples.

The water pressure resistance of the water-insoluble resin layer 42 is preferably at least 300 mm and more preferably at least 400 mm. This will allow the leakproofness of the water-insoluble resin layer 42 to be stably maintained. Also, the water pressure resistance of the water-insoluble resin layer 42 is preferably at least 300 mm and more preferably at least 400 mm after being stored for 3 hours under conditions of a temperature of 36° C. and a relative humidity of 90%. This will allow the leakproofness of the water-insoluble resin layer 42 to be stably maintained even in high humidity. An index of the water pressure resistance of the water-insoluble resin layer 42 is, for example, the water level (mm) measured according to "Method A (Low hydraulic pressure test)" of JIS L 1092:2009 7.1.1, and more specifically, the water level (mm) at which water leaks at three locations on the back side of a test piece.

The panty liner 1 exhibits the following effects during use and after disposal.

[During Use]

Liquid excreta of the user are absorbed by the water-disintegratable absorbent layer 41. The water absorption of the water-disintegratable absorbent layer 41 (300 g/m$^2$ or greater) is a sufficient amount of water absorption for commonly used panty liners. The water-disintegratable absorbent layer 41 disintegrates by the absorbed liquid excreta and decreases in strength, but the water-insoluble resin layer 42 has water resistance and therefore does not decrease in strength. Consequently, the water-disintegratable absorbent layer 41 is reinforced by the water-insoluble resin layer 42 and retains its form, allowing liquid excreta to be continuously absorbed.

Since the liquid excreta absorbed into the water-disintegratable absorbent layer 41 cannot pass through the water-insoluble resin layer 42, leakage of liquid excreta absorbed into the water-disintegratable absorbent layer 41 is prevented by the water-insoluble resin layer 42. The water resistance of the water-insoluble resin layer 42 is not affected by water in the liquid excreta absorbed into the water-disintegratable absorbent layer 41 and moisture in the air contacted by the water-insoluble resin layer 42, and therefore the leakproofness of the water-insoluble resin layer 42 is stably maintained.

The absorber 4 of the panty liner 1 therefore exhibits excellent leakproofness.

Since the absorber 4 exhibits leakproofness by itself, it is not necessary for the back sheet 3 of the panty liner 1 to be given a leakproof function. The back sheet 3 may of course be given a leakproof function, which will further increase the leakproofness of the panty liner 1.

Since it is not necessary for the back sheet 3 to be given a leakproof function, the back sheet 3 can be given a different function. For example, providing the back sheet 3 with an aerating function can prevent mustiness of the panty liner 1 when it is worn. Generally speaking, the absorption required for a panty liner may be less than the absorption required for a sanitary napkin or diaper, and therefore mustiness can be prevented by reducing the amount of absorber 4, providing a space between the top sheet 2 and the back sheet 3, and allowing air to flow between the space and the back sheet 3.

[After Disposal]

When the panty liner 1 is disposed, it is subjected to the force of water streams in flush toilets, wastewater treatment tanks, sewage systems and the like. The water stream force causes the water-disintegratable absorbent layer 41 to rapidly disintegrate and disappear. The water-insoluble resin layer 42 has the tear strength of 0.15 N/40 mm or less in both the first direction and the second direction perpendicular to the first direction, and disintegrates when subjected to a greater force by water stream. When the water-disintegratable absorbent layer 41 disappears, the water-insoluble resin layer 42 is also subjected to water stream force from the side where the water-disintegratable absorbent layer 41 was present, and therefore is easy to disintegrate.

The absorber 4 of the panty liner 1 therefore exhibits excellent water-disintegratability. For example, the absorber 4 exhibits water-disintegratability such that the dispersion ratio is 50 mass % or more when shaken in water for 48 hours at a shaking speed of 240 rpm.

Since both the top sheet 2 and the back sheet 3 of the panty liner 1 are water-disintegratable, they rapidly disintegrate under the force of water streams in flush toilets, wastewater treatment tanks and sewage systems. The panty liner 1 therefore entirely disintegrates in water. As a result, the disposed panty liner 1 does not easily clog up pipings or wastewater treatment tanks. When the water-insoluble resin layer 42 is biodegradable, it is decomposed by microorganisms.

EXAMPLES

Examples 1 to 5 and Comparative Examples 1 to 4

(1) Preparation of Example Product 1

As an absorbent layer, there was used a water-disintegratable airlaid nonwoven fabric comprising 80 wt % softwood kraft pulp (NBKP) and 20 wt % polyacrylic acid binder, and having a basis weight of 60 g/m$^2$.

As a material of a resin layer, there was used polylactic acid resin corresponding to a water-insoluble resin. The polylactic acid resin was biodegradable.

Polylactic acid resin (Terramac resin by Unitika, Ltd.) was melt extruded at 260° C. to obtain a polylactic acid resin layer having a film thickness of 10 μm, and the polylactic acid resin layer (100 wt % polylactic acid resin) was directly laminated on the airlaid nonwoven fabric to prepare an absorber sample (Example Product 1).

The thickness of the resin layer was measured using a PEACOCK PDN-20 by Ozaki Manufacturing Co., Ltd. (measuring terminal diameter: ϕ8 mm). The same was used for the other examples and comparative examples.

(2) Preparation of Example Product 2

An absorber sample (Example Product 2) was prepared in the same manner as Example Product 1, except that the film thickness of the polylactic acid resin layer was 15 μm.

(3) Preparation of Example Product 3

An absorber sample (Example Product 3) was prepared in the same manner as Example Product 1, except that the basis weight of the water-disintegratable airlaid nonwoven fabric was 30 g/m$^2$.

(4) Preparation of Example Product 4

An absorber sample (Example Product 4) was prepared in the same manner as Example Product 1, except that the basis weight of the water-disintegratable airlaid nonwoven fabric was 100 g/m$^2$.

(5) Preparation of Example Product 5

An absorber sample (Example Product 5) was prepared in the same manner as Example Product 1, except that the material of the resin layer was a blended resin comprising a dry blend of 70 wt % polylactic acid (ECODEAR by Toray Co., Ltd.) and 30 wt % polybutylene adipate/terephthalate (ECOFLEX by BASF). For the dry blending, the different pellets were first mixed and then melt mixed.

(6) Preparation of Comparative Example Product 1

As an absorbent layer, there was used a water-disintegratable non-crepe tissue with a basis weight of 15 g/m$^2$, comprising 50 wt % softwood kraft pulp (NBKP) and 50 wt % hardwood kraft pulp (LBKP).

As a material of a resin layer, there was used polyvinyl alcohol resin corresponding to a water-soluble resin. The polyvinyl alcohol resin was biodegradable in addition to being water-soluble.

Polyvinyl alcohol resin (ECOMATI AX by Nippon Synthetic Chemical Industry Co., Ltd.) was melt extruded at about 230° C. to obtain a polyvinyl alcohol resin layer having a film thickness of 17 μm, and the polyvinyl alcohol resin layer was directly laminated onto the water-disintegratable non-crepe tissue. Next, a silicone-based water-repellent agent (KS-3705 by Shin-Etsu Chemical Co., Ltd.) containing 5 wt % of a platinum catalyst was gravure printed onto the polyvinyl alcohol resin layer to a basis weight of 1 g/m$^2$, and then irradiated with ultraviolet ray for curing, and hot air dried to prepare an absorber sample (Comparative Example Product 1).

(7) Preparation of Comparative Example Product 2

An unstretched polylactic acid resin film (Comparative Example Product 2) was prepared by forming a film of a polylactic acid resin (ECODEAR by Toray Co., Ltd.) to a film thickness of 20 μm using a T-die.

(8) Preparation of Comparative Example Product 3

An absorber sample (Comparative Example Product 3) was prepared in the same manner as Example Product 1, except that the film thickness of the polylactic acid resin layer was 20 μm.

(9) Preparation of Comparative Example Product 4

An absorber sample (Comparative Example Product 4) was prepared in the same manner as Example Product 1, except that the basis weight of the water-disintegratable airlaid nonwoven fabric was 20 g/m$^2$.

(10) Evaluation test for Example Products 1 to 5 and Comparative Example Products 1 to 4

The tear strengths, water-disintegratabilities (dispersion ratios, visual), water pressure resistances, water pressure resistances after high humidity storage and water absorptions of Example Products 1 to 5 and Comparative Example Products 1 to 4 were evaluated by the following methods.

<Tear Strength>

The tear strength of the sample in the MD direction and the CD direction were measured according to the "Tear Test" of JIS K 6772:1994 7.5.

The specific procedure was as follows.

(a) A 40 mm width×150 mm length sample was prepared.
(b) A notch with a length of 75 mm was formed from the center of the short side of the sample, parallel to the long side.

(c) The notched strip was held with a tensile tester and the tensile strength was measured at a pull rate of 200 mm/min.
(d) The maximum strength was recorded as the tear strength (N/40 mm) of the sample.

<Water-Disintegratability>

The water-disintegratability of the sample was evaluated by the shake-flask method.

The procedure for the shake-flask method was as follows.
(a) A sample (100 mm×100 mm) was placed in a 1000 mL flask containing 800 mL of distilled water and shaken in a shaker (SHKV-200, product of Iwaki) for 48 hours at a shaking speed of 240 rpm.
(b) The shaken sample was filtered with a 2-mesh wire mesh (wire diameter: 1.5 mm, opening: 11.2 mm, percentage of open area: 77.8%), and the dispersion ratio was calculated by the formula shown below, where $M_0$ is the dry mass of the sheet before the test and $M_1$ is the dry mass of the sheet fibers remaining on the wire mesh. The evaluation was made with N=3, and the average value was calculated.

Dispersion ratio (%)=100×$(M_0-M_1)/M_0$ immediately used for measurement of the water level (mm) at which water was released from 3 locations on the back side of the sample, according to JIS L 1092, and this was used as an index of the water pressure resistance after high-humidity storage. The evaluation was made with N=5, and the average value was calculated.

<Water Absorption>

The sample (100 mm×100 mm) was dipped in distilled water for 1 minute and then allowed to stand for 1 minute on a net for draining, the weight (g) of the sample after water absorption was measured, and the water absorption (g/m$^2$) was calculated based on the difference between that value and the weight (g) of the sample before water absorption. The draining net used was a 250 mesh nylon net (N-No. 250HD by NBC Meshtec, Inc.).

The evaluation results are shown in Table 1. The water absorption of Comparative Example 1 could not be measured because the binder dissolved and disintegrated when dipped into the distilled water.

TABLE 1

|  |  |  | Example Product | | | | | Comparative Example Product | | | |
| --- | --- | --- | --- | --- | --- | --- | --- | --- | --- | --- | --- |
|  |  |  | 1 | 2 | 3 | 4 | 5 | 1 | 2 | 3 | 4 |
| Absorbent layer | Type |  | Water-disintegratable air-laid nonwoven fabric | | | | | Water-disintegratable tissue (non-crepe) | — | Water-disintegratable air-laid nonwoven fabric | |
|  | Basis weight (g/m$^2$) |  | 60.0 | 60.0 | 30.0 | 100.0 | 60.0 | 15.0 | — | 60.0 | 20.0 |
| Resin layer | Type |  | PLA | PLA | PLA | PLA | PLA/PBAT (70/30) | PVA laminate + silicone coating | PLA | PLA | PLA |
|  | Thickness (μm) |  | 10.0 | 15.0 | 10.0 | 10.0 | 10.0 | 18.0 | 20.0 | 20.0 | 10.0 |
| Absorber | Basis weight (g/m$^2$) |  | 70.0 | 75.0 | 40.0 | 110.0 | 70.0 | 33.0 | 20.0 | 80.0 | 30.0 |
|  | Tearing strength (N/40 mm) | MD direction | 0.045 | 0.110 | 0.105 | 0.105 | 0.062 | 0.148 | 0.185 | 0.213 | 0.041 |
|  |  | CD direction | 0.055 | 0.120 | 0.098 | 0.098 | 0.075 | 0.166 | 0.190 | 0.222 | 0.049 |
|  | Water-disintegratability | Dispersed state | A | B | B | B | A | A | C | C | A |
|  |  | Dispersion ratio (%) | 90 | 63 | 65 | 65 | 80 | 95 | 5 | 48 | 92 |
|  | Water pressure resistance (mm) |  | 340 | 405 | 480 | 480 | 570 | 350 | 635 | 670 | 310 |
|  | Water pressure resistance after high-humidity storage (mm) |  | 340 | 410 | 495 | 495 | 565 | 50 | 640 | 655 | 305 |
|  | Water absorption (g/m$^2$) |  | 865 | 862 | 385 | 1264 | 871 | Unmeasurable | — | 871 | 263 |

(c) Separately from (b), the dispersed state of the shaken sample was also evaluated visually. The evaluation was made with N=3, and the average value was calculated.

The evaluation criteria were as follows.

A: Dispersed to a level such that the original form was not maintained.

B: Dispersed into three or more portions, while partially maintaining the original form.

C: The original form was maintained.

<Water Pressure Resistance>

The water pressure resistance of the sample was determined according to JIS L 1092:2009 7.1.1 "Method A (Low hydraulic pressure test)", by measuring the water level (mm) at which water was released from 3 locations on the back side of the sample, and using this as an index of the water pressure resistance. The evaluation was made with N=5, and the average value was calculated.

<Water Pressure Resistance after High-humidity Storage>

After storing the sample for 3 hours under conditions with a temperature of 36° C. and a relative humidity of 90%, it was Example Products 1 to 5 satisfy all of the criteria listed below, and had both water resistance and water-disintegratability. In contrast, Comparative Example Products 1 to 4 failed to satisfy one or more of the criteria, and did not have both water resistance and water-disintegratability.

Tear strength in the MD direction of 0.15 N/40 mm or less.
Tear strength in the CD direction of 0.15 N/40 mm or less.
A dispersed state of A or B.
A dispersion ratio of 50% or more.
A water pressure resistance of 300 mm or more.
A water pressure resistance of 300 mm or more after high-humidity storage.
A water absorption of 300 g/m$^2$ or more.

Explanation Of Symbols

1 Panty liner (absorbent article)
2 Top sheet (first water-disintegratable sheet with liquid permeability)
3 Back sheet (second water-disintegratable sheet)
4 Absorber
41 Water-disintegratable absorbent layer
42 Water-insoluble resin layer

The invention claimed is:

1. An absorbent article comprising:
a first water-disintegratable sheet that has liquid permeability,
a second water-disintegratable sheet and
an absorber situated between the first water-disintegratable sheet and the second water-disintegratable sheet,
the absorber comprising a laminate of a water-disintegratable absorbent layer and a water-insoluble resin layer and being distinct from the first water-disintegratable sheet and the second water-disintegratable sheet,
wherein the water-disintegratable absorbent layer has a water absorption of 300 g/m$^2$ or more, and
the absorber has a tear strength of 0.15 N/40 mm or less measured according to JISK 6772:1994 7.5 in first and second directions on a surface of the water-insoluble resin layer, the second direction being perpendicular to the first direction.

2. An absorbent article according to claim 1, wherein the water-insoluble resin layer has a tear strength of 0.10 N/40 mm or less in the first and second directions.

3. An absorbent article according to claim 1, wherein the water-disintegratable absorbent layer is directly stacked on the water-insoluble resin layer.

4. An absorbent article according to claim 1, wherein the water-insoluble resin layer is biodegradable.

5. An absorbent article according to claim 1, wherein the water-insoluble resin layer has a water pressure resistance of 300 mm or more.

6. An absorbent article according to claim 1, wherein the water-insoluble resin layer has a water pressure resistance of 300 mm or more after storage for 3 hours under conditions of a temperature of 36° C. and a relative humidity of 90%.

7. An absorbent article according to claim 1, wherein the water-disintegratable absorber has a dispersion ratio of 50 mass % or more when shaken in water for 48 hours at a shaking speed of 240 rpm.

8. An absorbent article according to claim 1, wherein the water-insoluble resin layer has a thickness of 10 to 15 μm.

9. An absorbent article according to claim 1, wherein the water-insoluble resin layer contains polylactic acid as a water-insoluble resin.

10. An absorbent article according to claim 1, wherein the water-disintegratable absorbent layer comprises water-dispersible fibers and a water-soluble binder.

11. An absorbent article according to claim 10, wherein the water-dispersible fibers have a fiber length of 20 mm or less.

12. An absorbent article according to claim 10, wherein the water-disintegratable absorbent layer has a fiber basis weight of 30 to 100 g/m$^2$.

13. An absorbent article according to claim 2, wherein the water-disintegratable absorbent layer is directly stacked on the water-insoluble resin layer.

14. An absorbent article according to claim 2, wherein the water-insoluble resin layer is biodegradable.

15. An absorbent article according to claim 3, wherein the water-insoluble resin layer is biodegradable.

16. An absorbent article according to claim 13, wherein the water-insoluble resin layer is biodegradable.

17. An absorbent article according to claim 2, wherein the water-insoluble resin layer has a water pressure resistance of 300 mm or more.

18. An absorbent article according to claim 3, wherein the water-insoluble resin layer has a water pressure resistance of 300 mm or more.

19. An absorbent article according to claim 13, wherein the water-insoluble resin layer has a water pressure resistance of 300 mm or more.

* * * * *